United States Patent
Chen et al.

(10) Patent No.: US 7,473,799 B2
(45) Date of Patent: Jan. 6, 2009

(54) PROCESS FOR THE PREPARATION OF SYNTHETIC RETINOIDS WITH DISUBSTITUTED ADAMANTYL RADICAL

(75) Inventors: Liqin Chen, Jiangsu (CN); Lei Tian, Jiangsu (CN); Xiaoquan Yao, Jiangsu (CN)

(73) Assignee: Nanjing University of Aeronautics and Astronautics, Jiangsu (CN)

( * ) Notice: Subject to any disclaimer, the term of this patent is extended or adjusted under 35 U.S.C. 154(b) by 0 days.

(21) Appl. No.: 11/699,704

(22) Filed: Jan. 29, 2007

(65) Prior Publication Data

US 2008/0108848 A1    May 8, 2008

(30) Foreign Application Priority Data

Nov. 2, 2006    (CN) .................. 2006 1 0097378

(51) Int. Cl.
*C07C 69/52* (2006.01)
(52) U.S. Cl. ..................................... 560/220
(58) Field of Classification Search .................. 560/220
See application file for complete search history.

(56) References Cited

U.S. PATENT DOCUMENTS 5,015,758 A * 5/1991 Pilgrim et al. ................ 560/56
5,532,388 A * 7/1996 Bouchard et al. ........... 549/510

OTHER PUBLICATIONS

Hiroyuki Kagechika et al., "Synthetic Retinoids: Recent Developments Concerning Structure and Clinical Utility", *Journal of Medicinal Chemistry*, pp. 5875-5883, Sep. 22, 2005, vol. 48, No. 19, American Chemical Society.
Raffaella Cincinelli et al., "A Novel Atypical Retinoid Endowed with Proapoptotic and Antitumor Activity", *Journal of Medicinal Chemistry*, pp. 909-912, 2003, vol. 46, No. 6, American Chemical Society.

* cited by examiner

*Primary Examiner*—Daniel M Sullivan
*Assistant Examiner*—Sadhakar Katakam
(74) *Attorney, Agent, or Firm*—Patterson, Thuente, Skaar & Christensen, P.A.

(57) ABSTRACT

A process for the preparation of disubstituted adamantine derivatives characterized by the factor that the aromatic receptors can be a series of halide anisole, phenol, toluene, naphthalene, thiophene, or furan and their substituted derivatives. The synthesized disubstituted adamantine derivatives were subsequently converted into a new class of synthetic retinoids of pharmaceutical importance.

13 Claims, No Drawings

PROCESS FOR THE PREPARATION OF SYNTHETIC RETINOIDS WITH DISUBSTITUTED ADAMANTYL RADICAL

RELATED APPLICATION

The present application claims priority to Chinese Application No. 200610097378.3 filed Nov. 2, 2006, the disclosure of which is incorporated herein in its entirety by reference.

BACKGROUND OF THE INVENTION

Small hydrophobic molecules such as steroid hormones and activated vitamins A and D control various biological phenomena, including growth, development, metabolism, and homeostasis, by binding to an activating specific nuclear receptors. Retinoids are natural and synthetic analogues of retinoic acid, an active metabolite of vitamin A, and are specific modulators of cell proliferation, differentiation, and morphogenesis in vertebrates. Modern medicinal chemistry of retinoids started in the 1970s (*Journal of Medicinal Chemistry*, 2005, 48:5875-5882 and references cited therein). One class of synthetic retinoids are derivatives of polyenecarboxylic acids or aromatic carboxylic acids which consists of three parts, that is, the hydrophobic aromatic ring, benzoic acid moiety, and the linking group between them. Retinoid therapy using synthetic retinoids has already been realized in the field of dermatology and oncology. The synthetic retinoids, such as adapalene (compound 1) has been proven to be clinically useful in the treatment of acne and psoriasis.

Similar to adapalene, a number of other active compounds such as compound 2 (*Journal of Medicinal Chemistry*, 2003, 46:909-912 with 1-adamantyl radical in the molecules also have therapeutic activity, including cancer chemopreventive effect. The known synthetic methods capable of producing these compounds employ 1-adamantanol as the starting material. However, this process generates disubstituted (1,2 or 1,3) adamantane as byproduct. After fine tuning the process, the disubstituted adamantane becomes the major product.

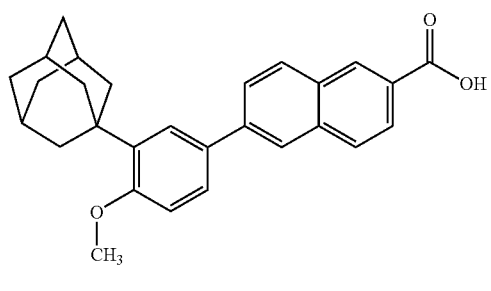

1

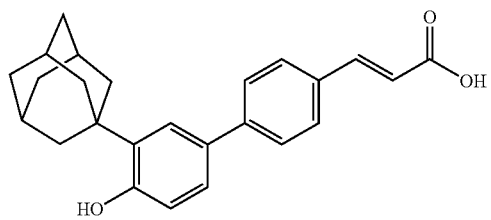

2

DETAILED DESCRIPTION OF THE INVENTION

The present invention offers a process for the preparation of disubstituted adamantine derivatives, which subsequently produce retinoids with disubstituted adamantyl radical that may be of pharmaceutical importance.

The process according to the invention is more specifically intended for the adamantylation of aromatic compounds, and in this case the receptor compound can, for example, be anisole, phenol, toluene, naphthalene, thiophene, or furan and their substituted derivatives.

According to a preferred embodiment, the aromatic receptor compounds have the general structures of 3 and 4, while the disubstituted adamantine derivatives have the general structures of 5 and 6, wherein R and X represent the substituent groups shown below.

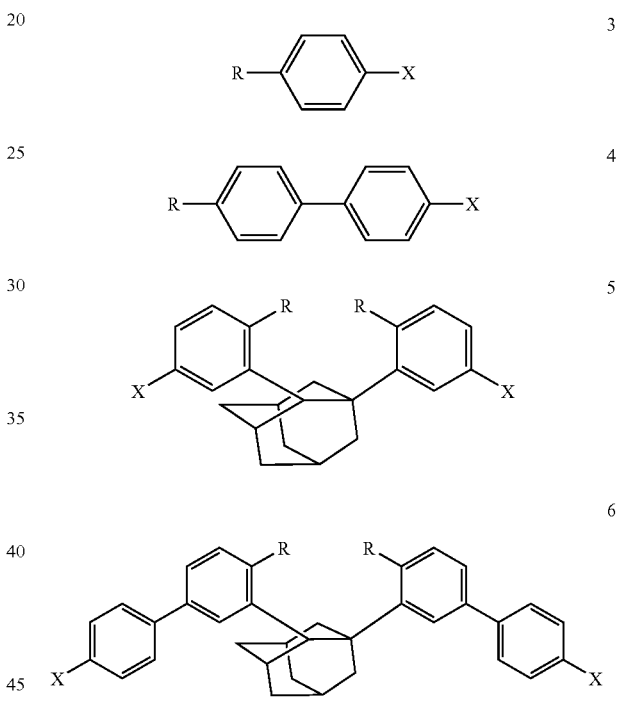

R=—OCH$_3$ X=Cl, Br, I, CN
—OH
—O(CH$_2$)$_5$CH$_3$
—CH$_2$OH
—(CH$_2$)$_3$OH
—CH$_2$CH(OH)CH$_2$OH
—COOH

The receptor compound can also be a thiol, in which case the process according to this invention leads to the formation of an adamantyl thioether. Among the thiols, special mention is made of 4-methoxy or 4-bromo benzene thiol.

The receptor compound can also be a nitrile such as acetonitrile. In this case the process according to the invention leads to the formation of an amide which can then be transformed under conventional conditions into 1,2-diaminoadamantane.

The following specific examples lead to the synthesis of a retinoid, compound 13 having dual structure of adapalene.

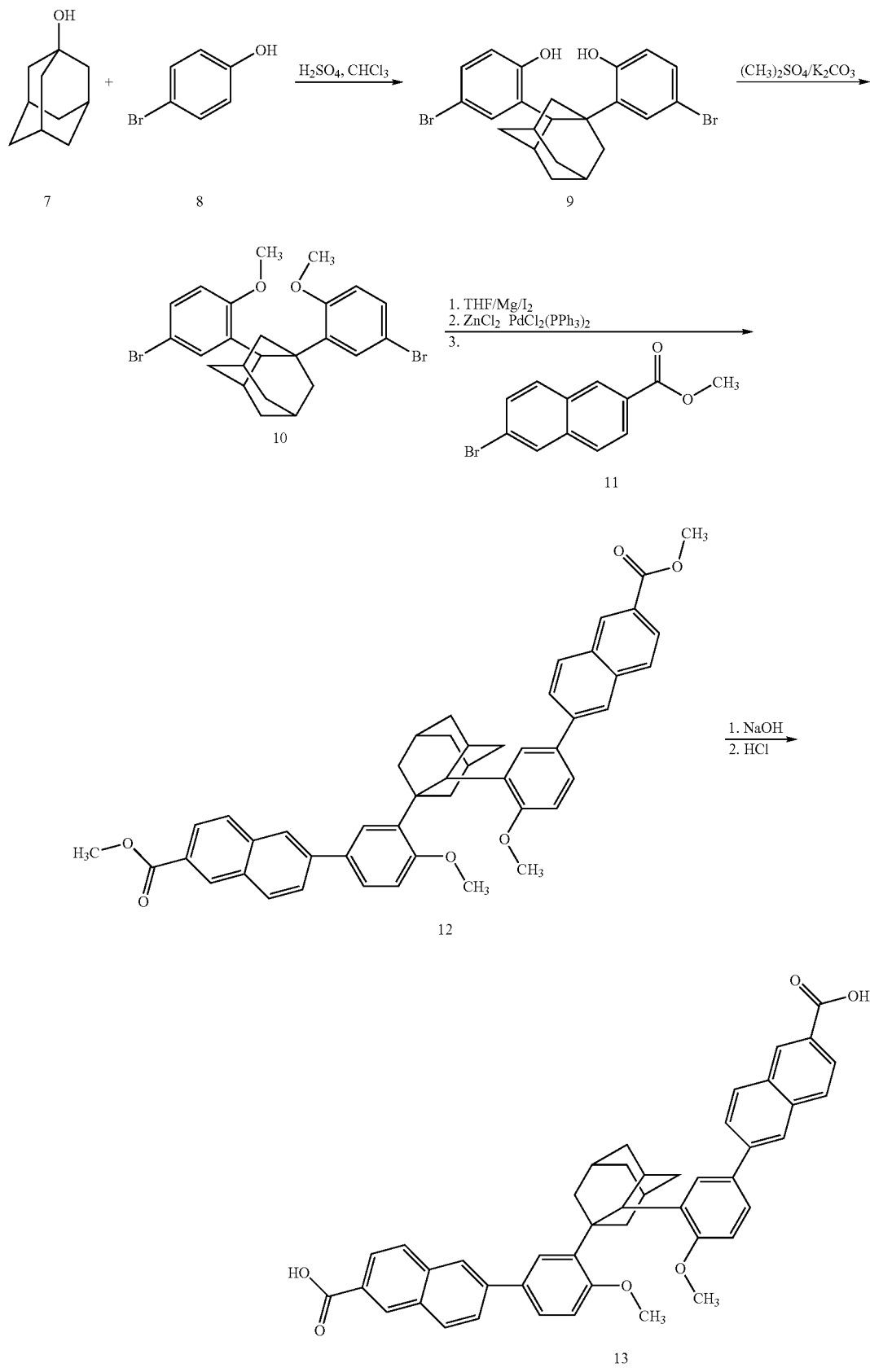

EXAMPLES

Compound 9: 7 (3.05 g, 0.020 mol) and 8 (8.65 g, 0.050 mol) were dissolved in $CH_2Cl_2$ (18 ml). Concentrated $H_2SO_4$ (1.07 ml, 0.020 mol) was added slowly to the resulting solution with the internal temperature at around 25° C. The resulting mixture was stirred at 25-30° C. for 3 hours, poured into water (100 ml), neutralized to pH 6 with saturated sodium carbonate solution, extracted with $CH_2Cl_2$ (3×100 ml). The organic phase was washed with water (2×100 ml), dried over anhydrous sodium sulfate, filtered. HPLC showed the solution contained about 30% compound 5, 70% compound 6. The solution was evaporated to dryness. The solid was purified by flash chromatography, eluted with the mixture of $CH_2Cl_2$ and methanol (95:5) to give 6.2 g pure light yellow solid compound 9 (99.5% HPLC). Yield 65%. The compound also can be obtained by recrystallizing the crude solid in chloroform and isooctane. The recovery was lower. The similar reaction conducted in chloroform at 40° C. offered compound 9 in 40% percent yield. $^1$H NMR(CDCl$_3$, 400 MHz): 7.33(s, 1H), 7.18(d, 1H), 6.55(d, 1H), 4.81(s, 1H), 2.42(s, 1H), 2.30(s, 1H), 2.19(d, 2H), 2.05(d, 2H), 1.79(s, 1H).

Compound 10: Dimethyl sulfate (2.0 ml, 0.021 mol) was added to a suspension of compound 9 (4.78 g, 0.010 mol) and anhydrous potassium carbonate (6.61 g, 0.063 mol) in dry acetone (100 ml). The mixture was reflux overnight, poured into water (200 ml), extracted with $CH_2Cl_2$ (2×100 ml). The organic layer was washed with 1M NaOH (2×100 ml) and brine (2×100 ml), dried over anhydrous sodium sulfate, filtered. To the filtrate was added heptane (200 ml) and concentrated. Off-white solid came out during concentration. The solid was filtered, washed with heptane to give 4.35 g compound 8 (98.5% HPLC). Yield 86%. $^1$H NMR(DMSO-d6, 400 MHz): 7.35(d, 1H), 7.20(s, 1H), 6.95(d, 1H), 3.79(s, 3H), 2.27(s, 1H), 2.20(s, 1H), 2.15(d, 2H), 1.87(d, 2H), 1.70(s, 1H).

Compound 12: A solution of compound 8 (2.53 g, 0.0050 mol) in THF (25 ml) was added dropwise under nitrogen to a stirred mixture of Mg turnings (0.292 g, 0.012 mol) and a small crystal of iodine in THF (5 ml) at 40° C. in 45 minutes. After addition, the mixture was maintained at 40° C. for 30 minutes. The resulting Grignard solution was then added directly to a stirred solution of methyl 6-bromo-2-naphthoate (compound 11) (3.18 g, 0.012 mol), $PdCl_2(PPh_3)_2$ (1.73 g, 0.0024 mol) and anhydrous $ZnCl_2$ (1.64 g, 0.012 mol) in dry THF (60 ml) at 50° C. in 10 minutes. The resulting mixture was stirred at 50-55° C. for 1 hour. The reaction was cooled in an ice bath and quenched by adding di-water (10 ml). The resulting paste was concentrated on a rotary evaporator and cooled in ice bath. 1 M HCl solution (100 ml) was added slowly. The suspension was extracted with $CH_2Cl_2$ (3×100 ml). The combined organic phase was dried over anhydrous sodium sulfate, filtered. The filtrate was evaporated to dryness and purified by flash chromatography, eluted with the mixture of $CH_2Cl_2$ and methanol (95:5) to give 2.45 g pure white solid compound 10 (99% HPLC). Yield 68%. $^1$H NMR(CDCl3, 400 MHz): 8.61(s, 1H), 8.00(m, 3H), 7.91(d, 1H), 7.81(d, 1H), 7.67(s, 1H), 7.57(d, 1H), 7.00(d, 1H), 3.99(s, 3H), 3.91(s, 3H), 2.60(s, 1H), 2.36(d, 3H), 2.17(d, 2H), 1.85(s, 1H).

Compound 13. Compound 10 (1.2 g, 0.0017 mol) was suspended in methanol (120 ml). The NaOH powder (0.34 g, 0.0084 ml) was added. The mixture was heated under reflux for 2 hours and concentrated to give a residue. 1 M HCl solution (50 ml) was added slowly to the residue. The off-white solid was filtered, washed with water and dried. The solid was recrystallized from THF to give 0.95 g off-white solid compound 2 (99% HPLC). Yield 81%. M-: 688. $^1$H NMR(DMSO-d6, 400 MHz): 12.82(b, 1H), 8.57(s, 1H), 8.19 (s, 1H), 8.14(d, 1H), 8.05(d, 1H),7.97(d, 1H), 7.89(d, 1H), 7.66(m, 2H), 7.14(d, 1H), 3.89(s, 3H), 2.53(s, 1H),2.34(m, 3H), 2.09(d, 2H),1.82(s, 1H).

The invention claimed is:

1. A process for the preparation of disubstituted adamantane derivatives comprising reacting a monosubstituted adamantane derivative with a halogentated aromatic receptor compound in a halogenated solvent in the presence of concentrated sulfuric acid at temperature between 5-60° C. to obtain an aromatically disubstituted adamantane derivative.

2. A process according to claim 1 wherein the monosubstituted adamantane derivative is selected from the group consisting of 1-adamanatol, 1-acyloxyadamantane, 1-formyloxyadamantane, 1-acetoxyadamantane and 1-propionyloxyadamantane.

3. A process according to claim 1 wherein the halogenated solvent is selected from the group consisting of dichloromethane, chloroform, and 1,2-dichloroethane.

4. A process according to claim 1 wherein the halogenated solvent is used in a proportion of between 5 and 100 times the quantity of the monosubstituted adamantane derivative.

5. A process according to claim 1 wherein the concentrated sulfuric acid and receptor are used in a portion of between 0.5:0.5:1 and 2.5:2.5:1 in relation to the quantity of the monosubstituted adamantane derivative.

6. A process according to claim 1 wherein the receptor is selected from the group consisting of halogentated anisole, halogentated phenol, halogentated toluene, halogentated naphthalene, halogentated thiophene, and halogentated furan.

7. A process according to claim 1 wherein the receptor is halogenated phenol.

8. A process according to claim 7 further comprising methylating the an aromatically disubstituted adamantane derivative.

9. A process according to claim 8, wherein the methylation agent is iodomethane or dimethyl sulfate.

10. A process according to claim 6 further comprising reacting the an aromatically disubstituted adamantane derivative of claim 6 with a halogenated aromatic compound in a double metal catalyzed coupling.

11. A process according to claim 10 wherein the halogenated aromatic compound is methyl 6-bromo-2-naphthoate.

12. A process according to claim 10 wherein the catalyst is $NiCl_2$(DPPE) or $PdCl_2(PPh3)_2$.

13. A process according to claim 10 further comprising hydrolysing one or more esters formed in claim 10 to give synthetic retinoic analogues.

* * * * *